(12) United States Patent
Miller et al.

(10) Patent No.: US 11,660,103 B2
(45) Date of Patent: *May 30, 2023

(54) METHODS AND SYSTEMS FOR ATTACHING TISSUE TO BONE

(71) Applicant: Medos International Sarl, Le Locle (CH)

(72) Inventors: Gerome O. Miller, Randolph, MA (US); Kevin B. McKenney, Needham, MA (US); Gregory R. Whittaker, Stoneham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 1397 days.

This patent is subject to a terminal disclaimer.

(21) Appl. No.: 15/782,045

(22) Filed: Oct. 12, 2017

(65) Prior Publication Data

US 2018/0028203 A1     Feb. 1, 2018

Related U.S. Application Data

(63) Continuation of application No. 13/328,656, filed on Dec. 16, 2011, now Pat. No. 9,788,844.

(51) Int. Cl.
*A61B 17/17*     (2006.01)
*A61B 17/04*     (2006.01)
*A61B 17/34*     (2006.01)

(52) U.S. Cl.
CPC .......... *A61B 17/17* (2013.01); *A61B 17/0401* (2013.01); *A61B 17/0483* (2013.01);
(Continued)

(58) Field of Classification Search
CPC ............ A61B 17/0401; A61B 17/0466; A61B 17/0474; A61B 17/0482; A61B 17/0483;
(Continued)

(56) References Cited

U.S. PATENT DOCUMENTS

| | | |
|---|---|---|
| 5,015,247 A | 5/1991 | Michelson |
| 5,250,055 A | 10/1993 | Moore et al. |

(Continued)

FOREIGN PATENT DOCUMENTS

| | | |
|---|---|---|
| DE | 19537747 A1 | 4/1997 |
| JP | 2010521195 A | 6/2010 |

OTHER PUBLICATIONS

Australian Office Action for Application No. 2012261743, dated Oct. 10, 2013 (4 pages).

(Continued)

*Primary Examiner* — Jing Rui Ou

(57) ABSTRACT

A system and method for attaching tissue to bone are provided. In one embodiment, a system for attaching tissue to bone includes a suture, suture anchor, inserter tool, drill, and drill guide having an outer guide and an inner guide. A method for attaching tissue to bone includes attaching a suture to tissue, nesting the suture in a notch on the distal end of the outer guide, passing the suture through a lumen formed in the outer guide, and inserting an inner guide in a lumen formed in the outer guide. The drill guide protects the suture from rotational movement of the drill and allows a user to maintain alignment between the drill guide and the drilled hole. As a result, a suture anchor can be more easily positioned within the drilled hole.

15 Claims, 15 Drawing Sheets

(52) U.S. Cl.
CPC .......... *A61B 17/0485* (2013.01); *A61B 17/34* (2013.01); *A61B 2017/044* (2013.01); *A61B 2017/0409* (2013.01); *A61B 2017/0414* (2013.01); *A61B 2017/0445* (2013.01)

(58) Field of Classification Search
CPC .......... A61B 17/0485; A61B 17/0487; A61B 17/0488; A61B 17/10; A61B 17/15; A61B 17/151; A61B 17/152; A61B 17/154; A61B 17/155; A61B 17/157; A61B 17/158; A61B 17/16; A61B 17/1633; A61B 17/17; A61B 17/1714–1735; A61B 17/1742–1767; A61B 17/1771–1792; A61B 17/1796; A61B 17/34; A61B 17/3403; A61B 17/8645; A61B 17/8875–8894; A61B 2017/0403–0408; A61B 2017/0409; A61B 2017/0411–0416; A61B 2017/042–0464; A61B 19/201; A61B 90/03; A61B 2017/0414; A61B 2017/044; A61B 2017/0445; A61F 2002/0817–0894
See application file for complete search history.

(56) References Cited

U.S. PATENT DOCUMENTS

| | | |
|---|---|---|
| 5,441,502 A | 8/1995 | Bartlett |
| 5,484,437 A | 1/1996 | Michelson |
| 5,489,307 A | 2/1996 | Kuslich et al. |
| 5,505,732 A | 4/1996 | Michelson |
| 5,749,878 A | 5/1998 | Bracy et al. |
| 5,797,909 A | 8/1998 | Michelson |
| RE36,020 E | 12/1998 | Moore et al. |
| 5,944,739 A | 8/1999 | Zlock et al. |
| 5,948,001 A | 9/1999 | Larsen |
| 5,948,002 A | 9/1999 | Bonutti |
| 5,951,559 A | 9/1999 | Burkhart |
| 5,984,002 A | 11/1999 | Kido et al. |
| 6,013,083 A | 1/2000 | Bennett |
| RE36,974 E | 11/2000 | Bonutti |
| 6,200,322 B1 | 3/2001 | Branch et al. |
| 6,224,595 B1 | 5/2001 | Michelson |
| 6,325,804 B1 | 12/2001 | Wenstrom, Jr. et al. |
| 6,416,518 B1 | 7/2002 | DeMayo |
| 6,491,714 B1 | 12/2002 | Bennett |
| 6,547,800 B2 | 4/2003 | Foerster et al. |
| 6,929,606 B2 | 8/2005 | Ritland |
| 6,951,538 B2 | 10/2005 | Ritland |
| 7,033,363 B2 | 4/2006 | Powell |
| 7,431,722 B1 | 10/2008 | Michelson |
| 7,785,347 B2 | 8/2010 | Harvie et al. |
| 8,439,947 B2 | 5/2013 | Howard et al. |
| 8,911,474 B2 | 12/2014 | Howard et al. |
| 9,788,844 B2 | 10/2017 | Miller et al. |
| 2003/0236447 A1 | 12/2003 | Ritland |
| 2005/0049617 A1 | 3/2005 | Chatlynne et al. |
| 2006/0085012 A1 | 4/2006 | Dolan |
| 2006/0149280 A1* | 7/2006 | Harvie ............... A61B 17/0401 606/92 |
| 2006/0149370 A1 | 7/2006 | Schmieding et al. |
| 2006/0167479 A1 | 7/2006 | Morris et al. |
| 2006/0293693 A1 | 12/2006 | Farr et al. |
| 2006/0293710 A1 | 12/2006 | Foerster et al. |
| 2007/0162124 A1 | 7/2007 | Whittaker |
| 2007/0219557 A1 | 9/2007 | Bourque et al. |
| 2008/0058816 A1* | 3/2008 | Philippon .......... A61B 17/8888 606/326 |
| 2009/0312776 A1 | 12/2009 | Kaiser et al. |
| 2011/0015675 A1 | 1/2011 | Howard et al. |
| 2013/0158596 A1 | 6/2013 | Miller et al. |

OTHER PUBLICATIONS

Chinese Office Action for Application No. 201210545423.2 dated Dec. 23, 2015.

Japanese Office Action for Application No. 2012-273236, dated Nov. 29, 2016.

* cited by examiner

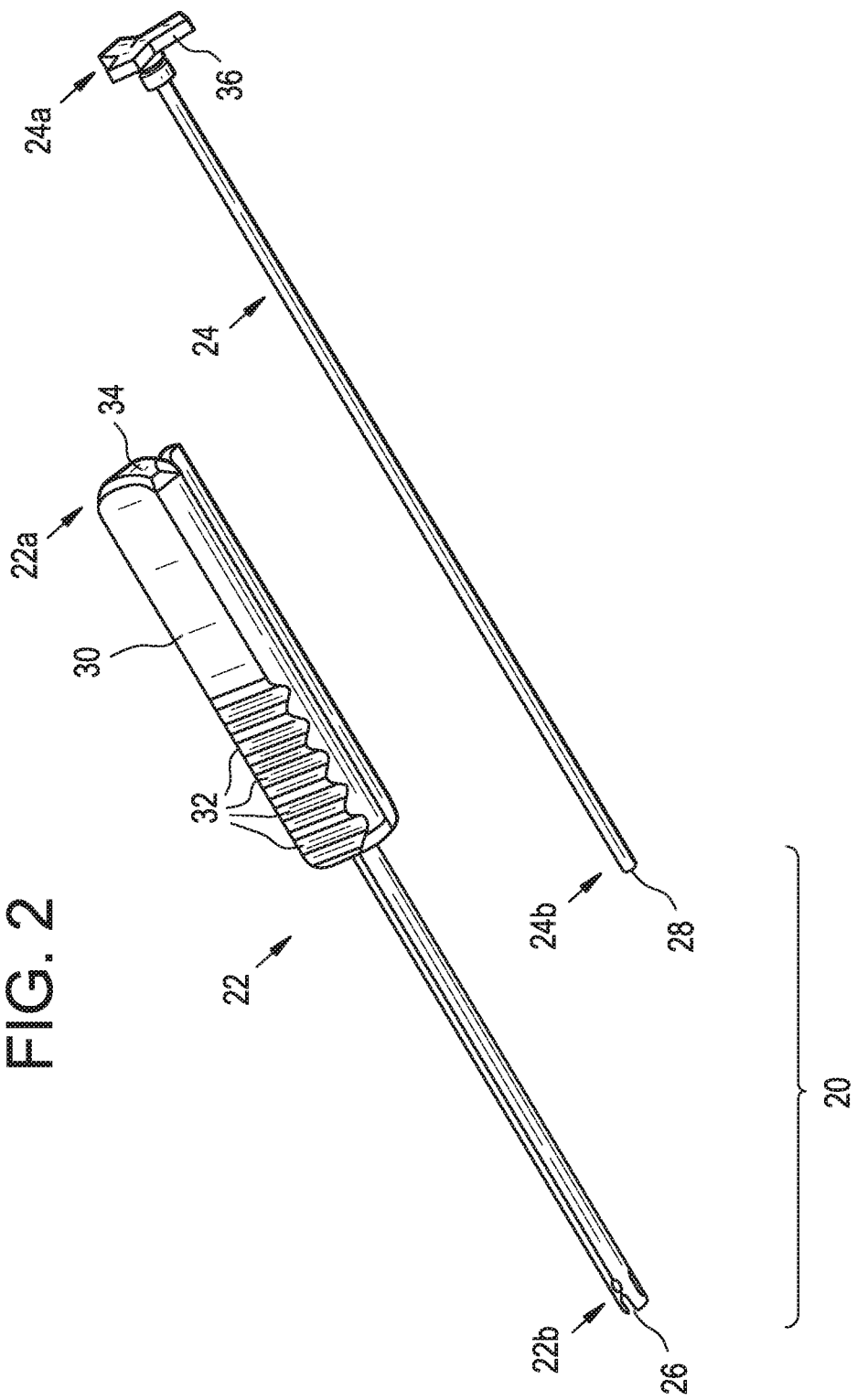

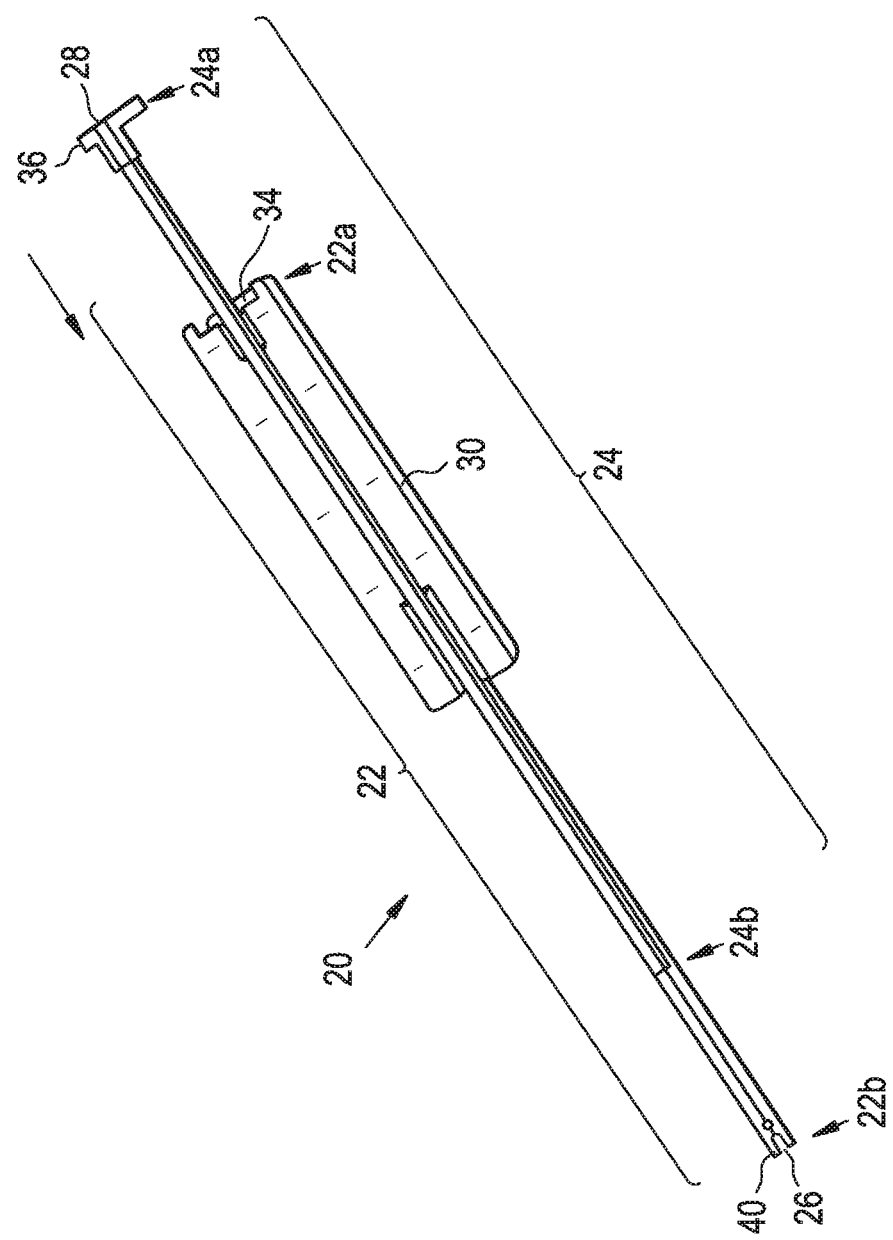

METHODS AND SYSTEMS FOR ATTACHING TISSUE TO BONE

CROSS REFERENCE TO RELATED APPLICATIONS

The present application claims priority to U.S. patent application Ser. No. 13/328,656 entitled "Methods and Systems for Attaching Tissue to Bone" filed Dec. 16, 2011, which is hereby incorporated by reference in its entirety.

BACKGROUND

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, or during the course of an athletic event. In the case of a partial detachment, the injury will frequently heal itself, if given sufficient time and if care is taken not to expose the injury to further undue stress. In the case of complete detachment, however, surgery is often needed to re-attach the soft tissue to its associated bone.

Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is drilled into the bone, through a drill guide, at the desired point of tissue re-attachment. Next, a suture anchor is deployed through the drill guide and into the hole using an appropriate installation tool. This effectively locks the suture to the bone, with the free end(s) of the suture extending out of the bone for attachment to soft tissue. The free ends of the suture are passed through or around the soft tissue and are used to secure the soft tissue to the bone.

While current suture anchoring methods are effective in anchoring soft tissue to bone, it can be difficult to deploy the suture anchor into the anchor-receiving hole, especially when a knotless suture anchor is used. For example, after the hole is formed in bone and the drill is removed from the surgical site, it can be difficult for a surgeon to locate the hole and navigate muscle and other bone to gain access to it. Even after the location of the hole is confirmed, it can be difficult to determine the angle of the hole. It is important that the location and angle of the drilled hole is accurately identified because forcing a suture anchor into the hole at an improper angle will often cause the anchor to fail. This can increase the time required to perform the tissue attachment procedure and increase costs.

Accordingly, there is a need for improved methods and systems for attaching tissue to bone.

SUMMARY

A system for attaching soft tissue to bone is disclosed herein. In general, the system includes a suture, suture anchor, and drill guide. The suture can have proximal and distal ends and a suture anchor can have an aperture for receiving a suture. In one embodiment, the drill guide comprises an outer drill guide and an inner drill guide. The outer drill guide can have a lumen formed therein that extends from a proximal end to a distal end. The inner drill guide can also have an inner lumen formed therein that extends from a proximal end to a distal end of the inner drill guide. Additionally, the inner drill guide can be configured to be removably and replaceably positioned within the lumen of the outer drill guide. When the inner drill guide is inserted into the lumen of the outer drill guide, the inner drill guide and outer drill guide are configured to retain at least a portion of the suture therebetween, and the suture is configured to slide relative to the inner and outer drill guides. In another embodiment, when the inner drill guide is inserted into the lumen of the outer drill guide, the distal end of the inner drill guide can terminate distal to the distal end of the outer drill guide. In yet another embodiment, when the inner drill guide is inserted into the lumen of the outer drill guide, the distal end of the inner drill guide can terminate proximal to the distal end of the outer drill guide. In another embodiment, the distal end of the outer drill guide can include at least one slot formed in a side wall thereof and extending proximally from the distal end.

The suture anchor and the drill guide can have a variety of other features. For example, the outer guide can further include at least one optional viewing window positioned adjacent to the at least one slot. Additionally, the distal end of the outer guide can have a plurality of surface features for engaging bone. In another embodiment, at least one bone engaging feature can be disposed on an outer surface of the suture anchor. In yet another embodiment, a proximal end of the inner guide can be configured to mate with the proximal end of the handle disposed on the outer guide.

The system can include a variety of other devices, such as a cannula, threader, and drill tool. The drill tool can be configured to be removably and replaceably positioned within the inner lumen of the inner drill guide, and a distal end of the drill tool can have a bone cutting tip disposed thereon. The threading tool can be configured to thread terminal ends of the suture through the lumen formed in the suture anchor. The cannula can have a central lumen that is configured to receive the outer guide therein.

A method of attaching soft tissue to bone is also disclosed herein. In one embodiment, a suture can be passed through tissue at a desired location within a patient's body such that the suture extends through the tissue and the first and second terminal ends of the suture are positioned outside of the patient's body. The outer guide can be positioned within the patient such that a distal end of the outer guide is located adjacent to bone at a location that will receive a suture anchor and such that a portion of suture extends through a central lumen of the outer guide. The suture can be attached to a suture anchor while terminal ends of the suture remain positioned outside of the patient's body. The inner guide can be inserted through the central lumen of the outer guide such that a portion of the suture is positioned between an outer wall of the inner guide and an inner wall of the outer guide. The bone drill can be inserted through a central lumen in the inner guide and can form a hole at a desired location in the bone and subsequently, the bone drill and the inner guide can be removed. While the outer guide is maintained in position surrounding the hole and in contact with bone, the suture anchor can be passed through the outer guide and implanted within the hole.

The method can include a variety of other steps. For example, in one embodiment, when the outer guide is positioned within the patient, a portion of the suture adjacent to the distal end of the outer guide is slidably nested in a notch that extends proximally from the distal end of the outer guide. In another embodiment, when the inner guide is inserted into the outer guide, the distal end of the inner guide terminates proximal to the distal end of the outer guide. This ensures that the suture can pass through the notch rather than being pinched between the distal end of the drill guide and bone. In another embodiment, attaching the suture to the suture anchor is accomplished by passing a portion of the suture from a position outside of the suture anchor, through an opening at a distal end of the suture anchor, and up through a central lumen within the suture anchor. In addition, attaching the suture to the suture anchor can be performed prior to inserting the bone drill through the central lumen in the inner guide. In yet another embodiment, the method includes tensioning the suture to draw the tissue into a desired position with respect to the bone. In another embodiment, positioning an outer guide within the patient includes passing a portion of the suture through the central lumen of the outer guide until the terminal ends of the suture are positioned outside of the outer guide. In another embodiment, positioning the outer guide within the patient includes positioning the outer guide through a cannula inserted in the patient. In yet another embodiment, when the suture anchor is passed through the outer guide, a longitudinal axis of the suture anchor is substantially aligned with a longitudinal axis of the anchor receiving hole. The method can further comprise trimming the suture adjacent to a proximal end of the suture anchor.

BRIEF DESCRIPTION OF THE DRAWINGS

The invention will be more fully understood from the following detailed description taken in conjunction with the accompanying drawings, in which:

FIG. 2 is a side view of one embodiment of a drill guide having an outer guide and an inner guide;

FIG. 4 is a cross-sectional view of the inner guide being inserted into the outer guide;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Systems and methods for attaching tissue to bone are disclosed herein. In one embodiment, a system for attaching tissue to bone includes a suture, suture anchor, inserter tool, drill, and a drill guide set. The drill guide set comprises an outer drill guide and an inner drill guide that is configured to be removably and replaceably received within a lumen of the outer drill guide. The inner drill guide also has a lumen that extends longitudinally therethrough and that is configured to receive a drill. In one embodiment, the outer drill guide can include a slot or notch extending proximally from the distal end thereof that is configured to receive a portion of suture therein. The notch protects the suture from rotational movement of the drill and prevents the suture from being trapped between an outer surface edge of the outer drill guide and adjacent bone.

A method for attaching soft tissue to bone is also provided. This method includes attaching a suture to tissue, passing a suture through a lumen formed in the outer drill guide, and inserting an inner drill guide into the lumen of the outer drill guide. The method further includes inserting a drill through a lumen in the inner drill guide, removing the inner drill guide, threading an anchor with the suture, and inserting it through the outer guide. The anchor and its attached suture are then seated in the prepared hole and the outer drill guide is removed. An advantage of this method is that alignment between the drilled hole and the drill guide can be maintained such that a suture anchor can be more easily inserted into the drilled hole.

A variety of tools can be used in practicing the method for attaching soft tissue to bone that is described herein. The types and designs for the various tools that assist in practicing this method are first described, followed by a discussion of the method for attaching soft tissue to bone.

Figure 1:
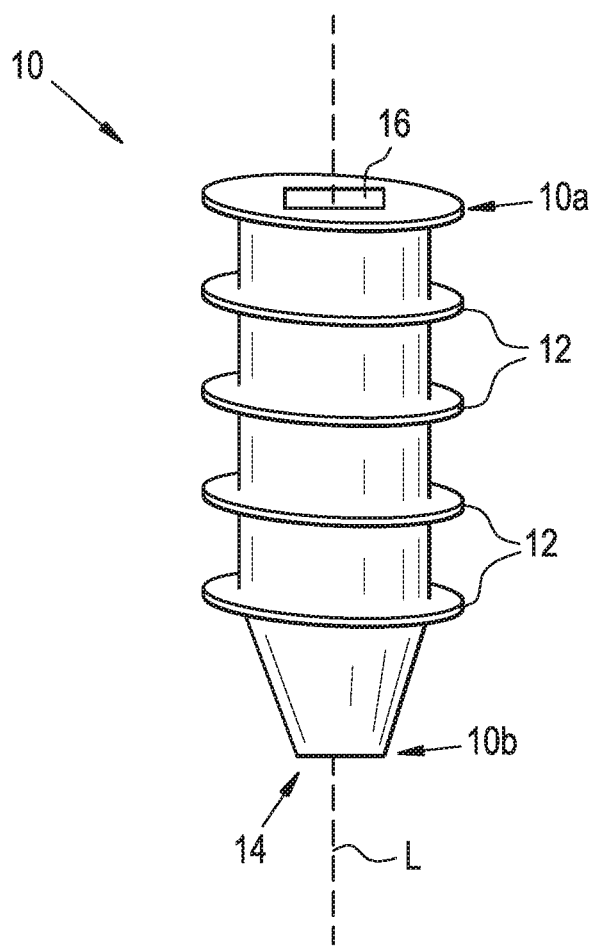
FIG. 1 is a side view of one embodiment of a suture anchor.

Suture anchors having a variety of different constructions can be used with the method disclosed herein. By way of example, FIG. 1 illustrates one embodiment of a suture anchor 10. As shown, the suture anchor 10 is generally elongate with a longitudinal axis L extending between a proximal end 10a and a distal end 10b. The suture anchor 10 can also have at least one feature, such as threads 12, configured to engage bone. The suture anchor 10 can also have features for receiving a suture therein. By way of non-limiting example, the suture anchor 10 of FIG. 1 can have an inner lumen 14 that extends between proximal and distal ends 10a, 10b, along a longitudinal axis L of the anchor 10, for receiving a suture. In another embodiment, an aperture (not shown) can extend at least partially through the anchor 10 along an axis transverse to longitudinal axis L. As will also be appreciated by a person skilled in the art, a suture anchor can alternatively have one or more apertures or openings disposed at any location on the anchor, such as on a sidewall of the anchor. Such apertures can form a pathway for receiving a suture that can be curved, or of any other shape. The suture anchor 10 can also be a knotless suture anchor that allows a user to thread the anchor with suture and form a loop without tying a knot. By way of non-limiting example, a suture (not shown) can be threaded through the anchor by inserting one terminal end of the suture through the proximal end 10a of the anchor, passing it distally, moving around a distal end 10b of the suture anchor, and out through a sidewall of the anchor. A suture threader (not shown) can also be used to thread the suture through suture anchor 10. The suture anchor 10 can also have a mating feature 16 positioned on the proximal end 10a of the anchor and configured to mate with a distal end of an inserter tool. A person skilled in the art will appreciate that the suture anchor can have a variety of configurations that can be threaded with a suture and engage bone.

A variety of drill guides can be used. For example, a drill guide set 20 is able to protect a suture during rotation of a drill that is inserted in the drill guide 20. As shown in FIG. 2, an exemplary drill guide set 20 generally comprises an outer guide 22 and an inner guide 24. Both the outer and inner guides 22, 24 are elongate and have proximal ends 22a, 24a and distal ends 22b, 24b with an inner lumen 26, 28 extending therebetween, respectively. The inner guide 24 can be configured to be removably and replaceably inserted into the lumen 26 formed in the outer guide 22. In the illustrated embodiment, a handle 30 is positioned on a proximal portion of the outer guide 22. The handle 30 can be elongate with a generally triangular cross-section and a plurality of surface features 32 that can provide friction between a user's hand and the handle. The proximal end of the handle 22a can also include a mating feature 34 for coupling the inner guide 24 to the outer guide 22, as will be described below. In the illustrated embodiment, the mating feature 34 is a recess formed on the proximal end 22a of the outer guide 22 that is mateable with a protrusion 36 formed on a proximal end 24a of the inner guide 24. A person skilled in the art will appreciate that the handle can have a variety of configurations and a variety of mating features can be used to couple the inner guide to the outer guide.

Figure 3A:
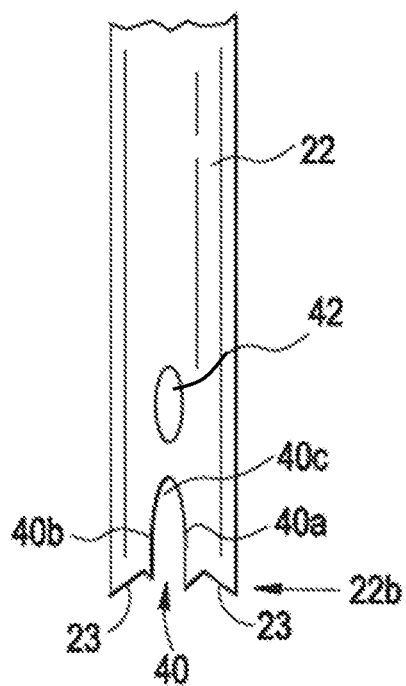
FIG. 3A is a side view of the distal end of the outer guide showing a notch and viewing window.
Figure 3B:
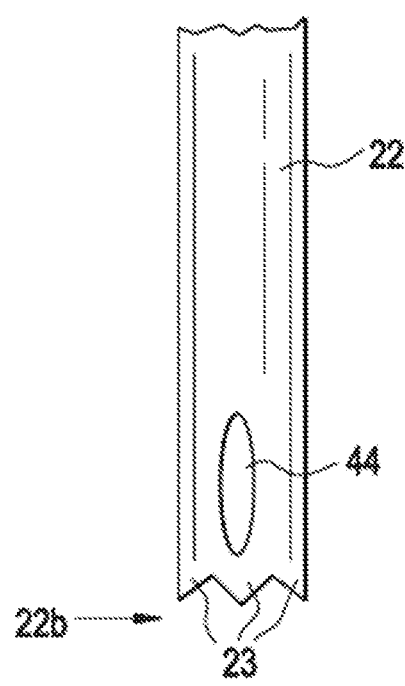
FIG. 3B is a side view of the distal end of the outer guide rotated by 90° and showing another viewing window.

The outer guide can include additional features, such as a notch and a viewing window. As shown in FIG. 3A, the distal end 22b of the outer guide 22 can have a notch 40 configured to receive limbs of a suture as they exit lumen 26. In the illustrated embodiment, the notch 40 extends proximally from the distal end 22b of the outer guide 22 and is elongate with two opposed sides 40a, 40b. In one embodiment, the notch 40 can terminate in an end 40c to reduce the risk of the suture being torn or damaged during tensioning of the suture. While the illustrated embodiment has another notch (not shown) positioned 180° offset from the notch 40, a person skilled in the art will appreciate that the outer guide 22 can include any number of notches positioned at any number of locations around the outer guide. A person skilled in the art will also appreciate that the outer guide 22 can have alternative features for protecting the suture from being torn or damaged during tensioning, and as a result, the outer guide 22 need not have notches. The distal end 22b of the outer guide 22 can also have a plurality of viewing windows spaced about the outer guide 22 that allow viewing of the inserter tool when the suture anchor is inserted into the drill guide. In one embodiment, the viewing window 42 shown in FIG. 3A is substantially elliptical and has a major axis that extends along a longitudinal axis of the outer guide 22. In this embodiment, four viewing windows can be provided. For example, smaller window 42 can be positioned proximal to the notch 40, and it can have a corresponding smaller window (not shown) that is directly opposite to it. A pair of larger windows can also be provided. In particular, larger window 44 can be positioned 90° offset from the notch 40, and it can also have a corresponding larger window (not shown) that is directly opposite to it. As will be appreciated by a person skilled in the art, the smaller window 42 can be positioned relative to the notch 40 by a predetermined distance that will enable viewing of a first laser line and a second laser line formed on a inserter tool within the windows 42 at certain stages of a surgical procedure, as discussed below. In particular, the viewing windows can be spaced at a predetermined distance from the distal end of the outer guide 22 such that when the inserter tool is inserted into the outer guide 22 and the suture anchor is partially seated in the drilled hole, the first laser line is visible within at least one of the viewing windows. The placement of viewing windows can also be such that when the anchor is fully seated in the drilled hole, the second laser line is visible in at least one of the viewing windows. A person skilled in the art will appreciate that the viewing windows can have a variety of configurations and any number of viewing windows can positioned at numerous locations about the outer guide.

A plurality of engagement features 23 can also be formed on the distal end 22b of the outer guide 22, serving to help maintain the guide in a desired position on bone. As will be appreciated by a person skilled in the art, such surface features can allow the outer guide to superficially penetrate the bone surface, such as by forming indentations to help seat the outer guide in bone.

Figure 10:
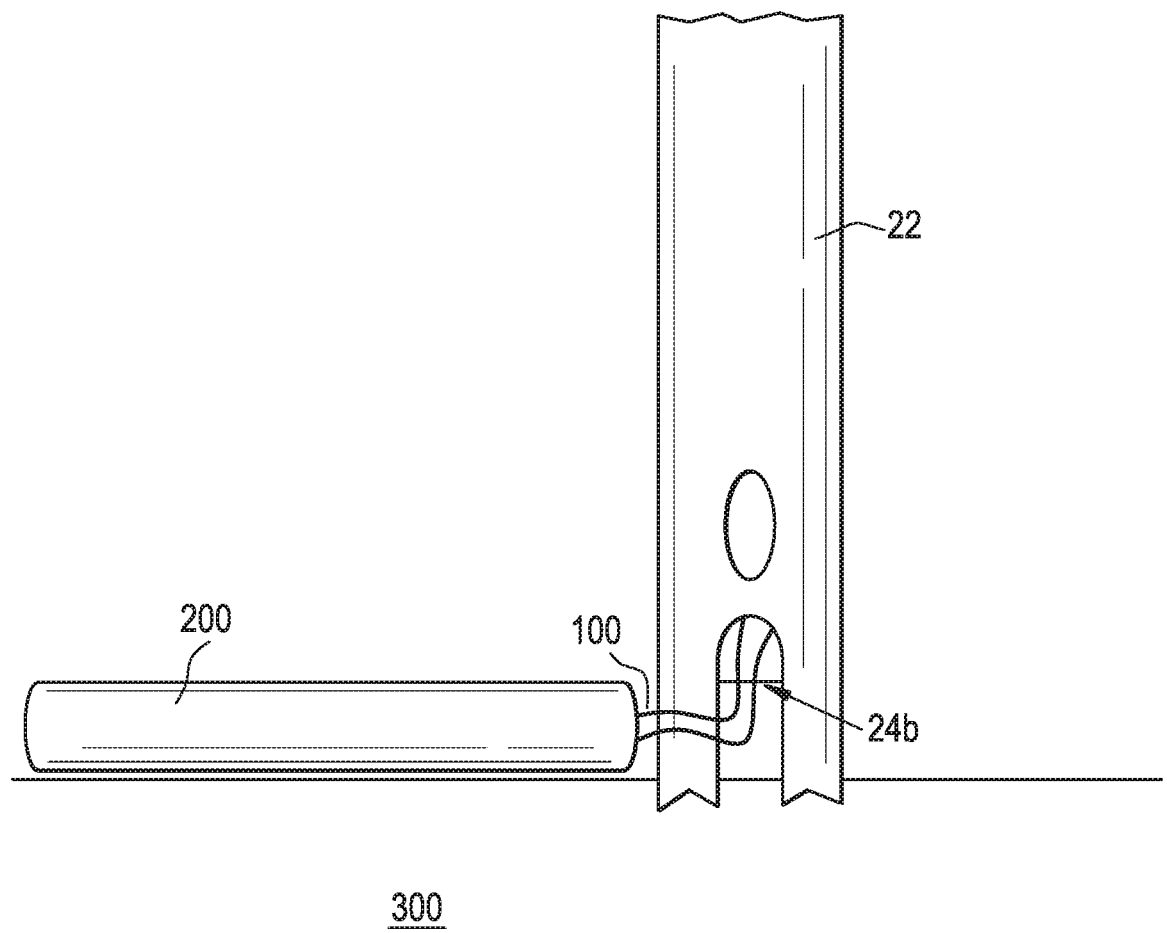
FIG. 10 is a side view of a distal portion of the drill guide with suture limbs extending through a notch formed in the outer guide.

As explained, the inner guide can be configured to be removably and replaceably inserted into the lumen 26 formed in the outer guide 22. FIG. 4 illustrates a cross-section of the drill guide 20 with the inner guide 24 being inserted into the outer guide 22. As shown, the outer guide 22 has an effective length greater than the effective length of the inner guide. In other words, when the inner guide 24 is operatively disposed within the outer guide 22, the portion of the inner guide 24 that is within the outer guide 22 has a length that is less than the length of the outer guide 22. Typically, the distal end 24b of the inner guide 24 terminates proximal to the distal end 22b of the outer guide 22. However, a person skilled in the art will appreciate that the outer and inner guides can have a variety of other configurations, and that the outer guide can have an effective length less than or equal to the inner guide. As shown, the inner guide 24 can also be configured to be positioned within the lumen 26 of the outer guide 22 such that a gap is formed between an outer wall of inner guide 24 and an inner wall of outer guide 22. This gap provides a space within which the suture 100 can reside and slide freely relative to the inner guide 24 and outer guide 22. In use, the distal end 24b of the inner guide 24 can be inserted through the proximal end 22a of the handle 30 until the protrusion 36 on the proximal end 24a of the inner guide 24 is seated in recess 34 formed on proximal end 22a of the handle 30. When the inner and outer guides 24, 22 are in this position, the distal end 24b of the inner guide 24 is just proximal or just distal to the transverse end 40c of the notch 40 as shown in FIG. 10. This ensures that a sufficient portion of the notch 40 is left open and unobstructed such that a suture can pass between the opposed sides 40a, 40b of the notch 40. And because the inner guide 24 extends along a substantial portion of the outer guide 22, the limbs of the suture proximal to the notch 40 are still protected between the inner and outer guides 24, 22. A person skilled in the art will appreciate that a variety of other features can be used to indicate that the distal end of the inner guide is positioned adjacent to the notch, such as having one or more markings on the inner and outer guides, and/or other components of the system, and a variety of mating features can be used to couple the inner guide to the outer guide.

Figure 5:
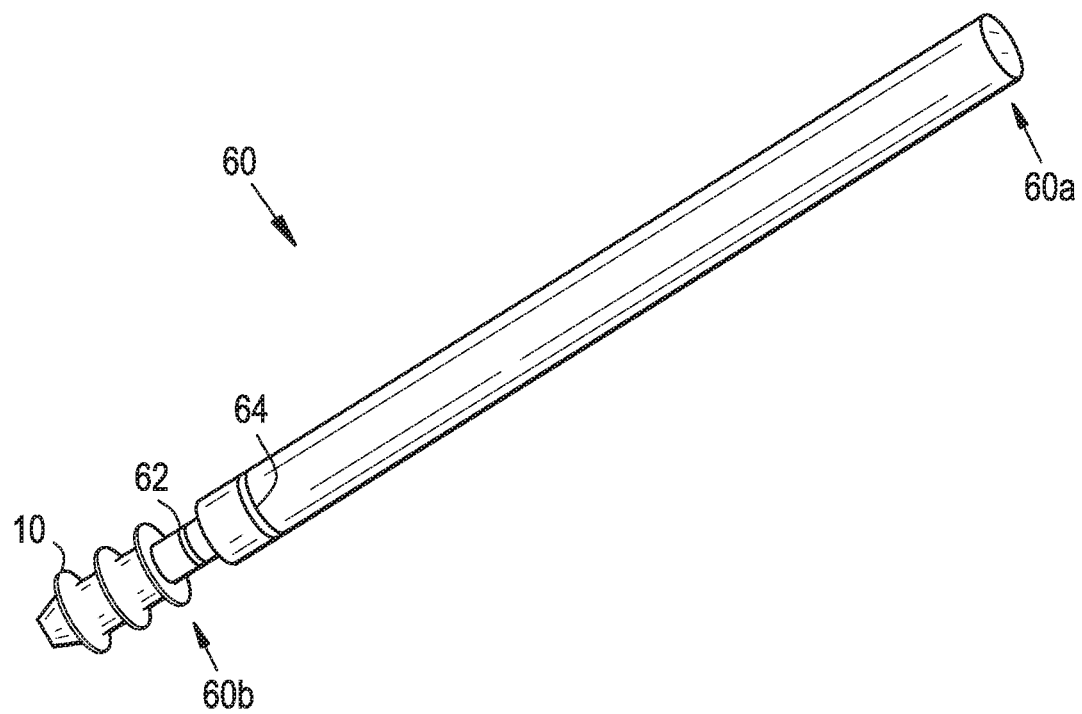
FIG. 5 is a side perspective view of an inserter tool mated to the suture anchor of FIG. 1.

Although a variety of suture anchor inserter tools can be used, an exemplary suture anchor inserter tool is shown in FIG. 5. Inserter tool 60 is elongate and is configured to be positioned within the lumen 26 of outer guide 22. The inserter tool 60 can have a length greater than the length of the outer guide 22 such that the anchor 10 can be deployed into an anchor receiving hole with a proximal end 60a of the inserter 60 being positioned outside of the drill guide 20. The distal end 60b of the inserter 60 can be configured to couple to a proximal end 10a of a suture anchor 10, such as by a mating feature (not shown) that corresponds to the recess 16 formed at the proximal end 10a of the anchor 10 and is aligned with a longitudinal axis of the anchor 10. As shown, the inserter tool 60 can further include a first laser line 62 and a second laser line 64 positioned proximal to the first laser line 62. The first laser line 62 and the second laser line 64 can be spaced a predetermined distance from the distal end of the inserter tool 60 such that laser lines 62, 64 are visible within viewing windows of outer guide 22 at certain stages of a surgical procedure, as will be explained below.

Figure 6:
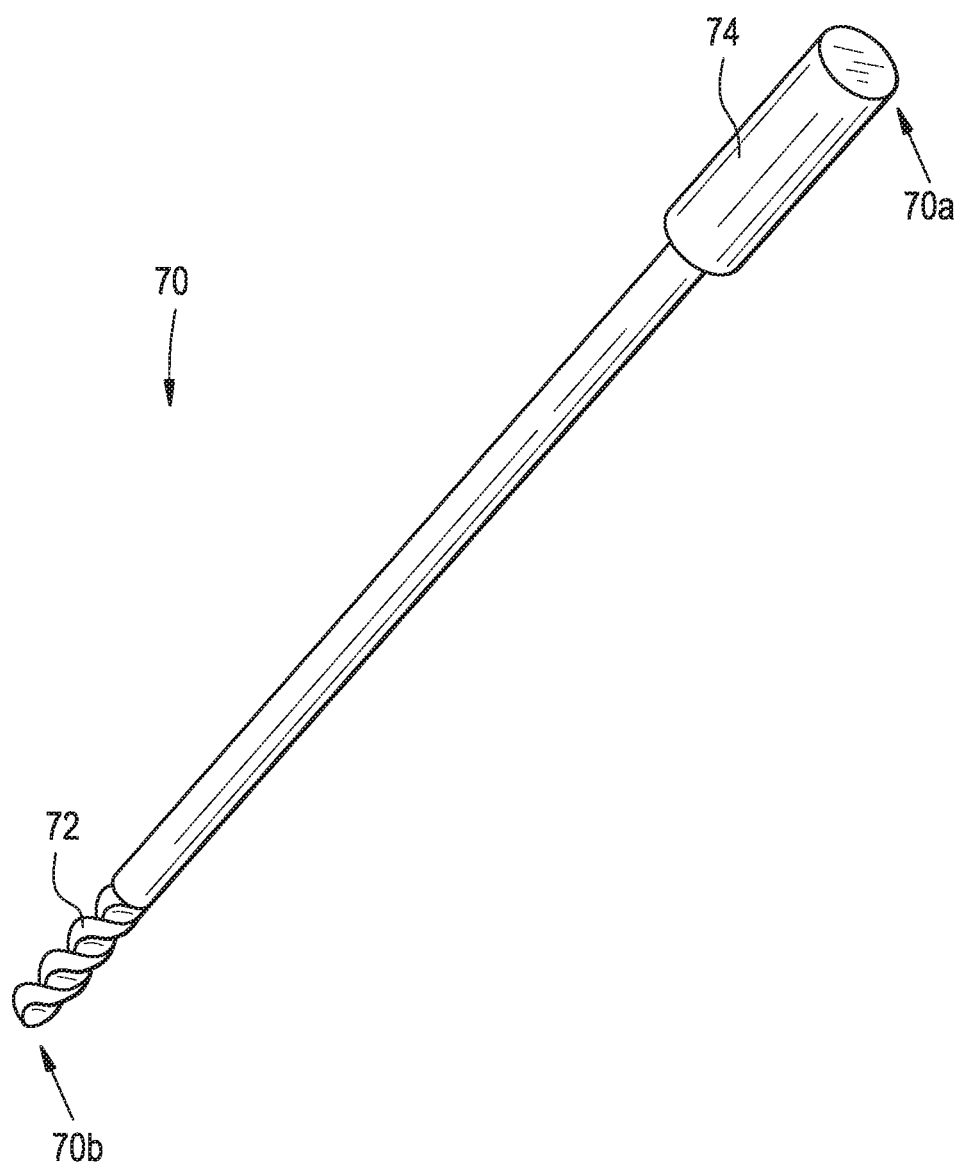
FIG. 6 is a side view of a drill, according to one exemplary embodiment.

While a variety of drills can be used to form a hole in bone, an exemplary embodiment is provided in FIG. 6. As shown, a drill 70 is elongate and has proximal and distal ends 70a, 70b. The distal end 70b of the drill 70 can include a cutting tip 72 configured to penetrate bone. The illustrated cutting tip 72 has a threaded outer surface that can be driven through bone and divert the drilled material away from the hole. The length of the drill 70 is typically greater than the length of the drill guide 20 such that when the drill 70 is inserted in the drill guide 20, the distal end 70b of the drill 70 can be advanced through bone and a handle 74 disposed on the proximal end 70a of the drill 70 can be grasped by a user. In the illustrated embodiment, the proximal end 70a of the drill 70 can be manually rotated by a user to thereby advance the cutting tip 72 through bone. Alternatively, a motor can be used to power the drill 70 to cause rotation of the cutting tip 72. A person skilled in the art will appreciate that the drill can have a variety of configurations that can form a hole in bone.

Figure 7:
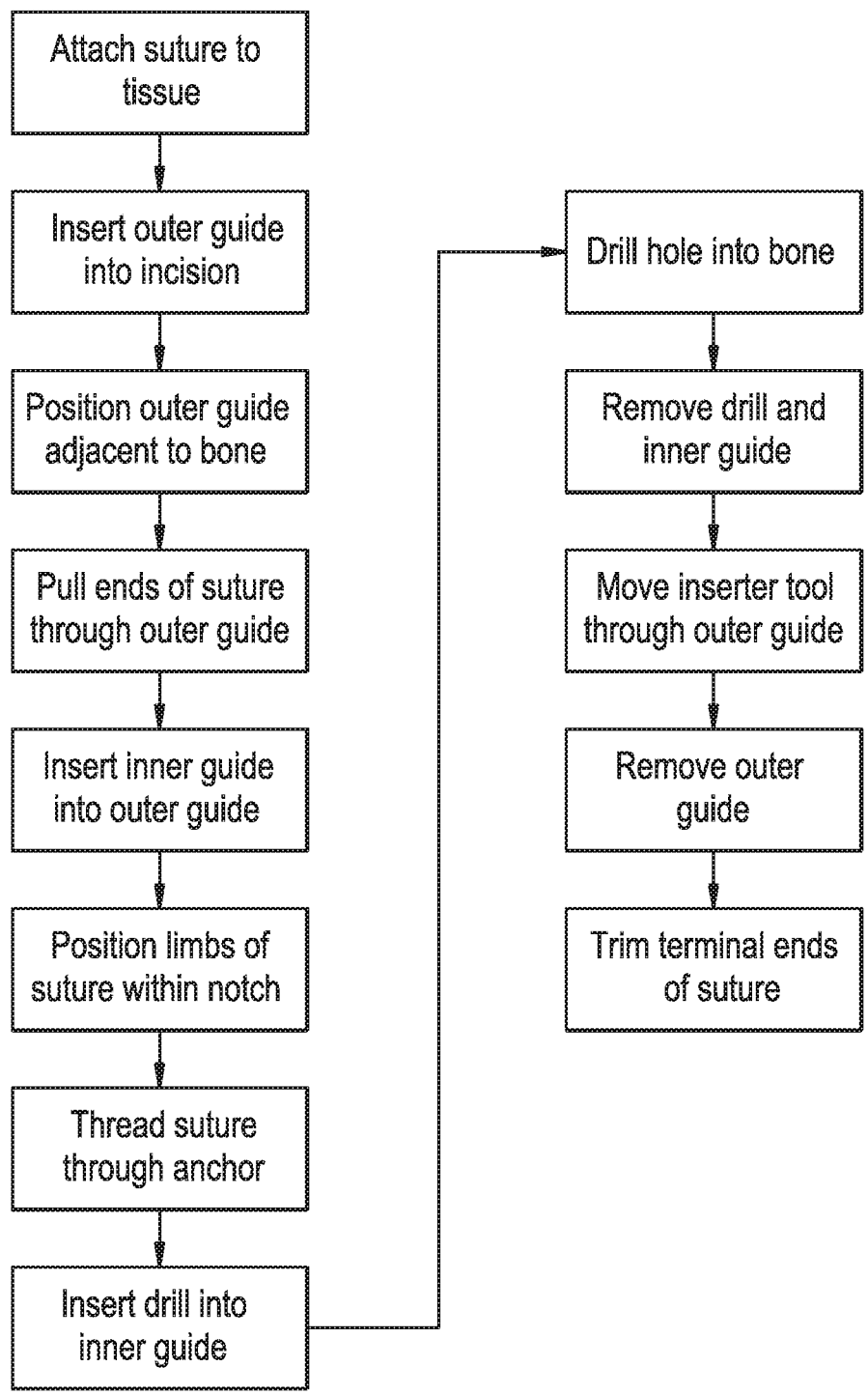
FIG. 7 is a flow chart that generally illustrates a method for attaching tissue to bone, according to one exemplary embodiment.

The devices described above can be used to perform a surgical procedure for attaching soft tissue to bone. One skilled in the art will understand that the procedure is ideally a minimally invasive procedure. A flow chart illustrating the general method for attaching tissue to bone is provided in FIG. 7. As one skilled in the art will appreciate, the procedure usually begins by preparing the patient for surgery and making one or more appropriately sized incisions at a desired location. In a minimally invasive procedure, one or more cannulas (not shown) can be positioned in the incisions to provide access to the surgical site. One skilled in the art will also understand that one or more viewing devices, e.g., scopes, can be placed in one of the incisions to allow medical personnel to view the surgical site from outside the body. Although a cannula is typically used, for clarity, the embodiments shown in FIGS. 8-15 illustrate the drill guide 20 being advanced directly into an incision, without being inserted through a cannula.

Figure 8:
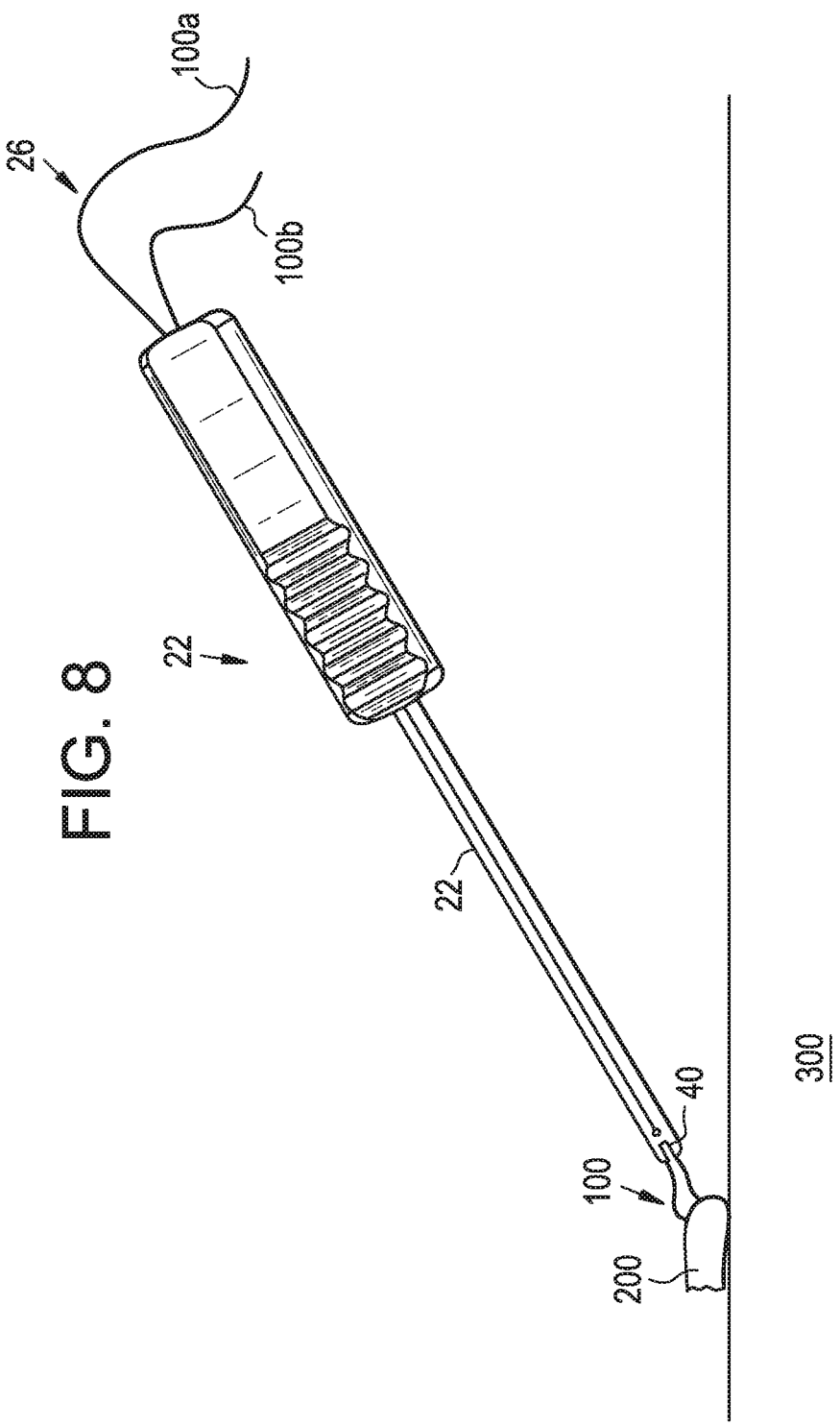
FIG. 8 is a side view of a suture attached to tissue and having limbs extending through the outer guide.

Once the patient is prepared for surgery, a length of suture 100 is passed into the patient's body and passed through soft tissue 200 that is to be surgically reattached to bone 300. As shown in FIG. 8, the suture 100 can be passed through tissue 200 such that the terminal ends 100a, 100b are positioned outside of the patient's body. One skilled in the art will appreciate that the suture can be passed through the tissue using any known surgical technique, such as by mattress and cinch loop methods. With the suture so positioned, the outer guide 22 is positioned within the surgical site with the suture 100 being positioned within the lumen 26 of the outer guide 22. This can be accomplished by a variety of well known techniques, including by passing the outer guide 22 over the suture 100 from a position outside of the patient's body. Alternatively, a suture passer (not shown) can be inserted into the lumen 26 of the outer drill guide 22 to retrieve the limbs of the suture 100. In particular, the limbs of the suture 100 can be grasped and moved proximally through the outer drill guide 22 until the terminal ends of the suture 100a, 100b are positioned outside of the outer drill guide 22.

FIG. 8 illustrates outer guide 22 positioned at the surgical site with the suture 100 extending therethrough. Optionally, once the suture 100 is positioned within the lumen 26 of outer guide 22, the suture limbs adjacent to the distal end 22b of the outer guide 22 can be passed through the notch 40 formed on the outer guide 22 to prevent the suture limbs from being pinched between the engagement features formed on the distal end 22b of the outer guide 22 and the adjacent bone 300. For example, this can be accomplished by rotating the outer guide 22 until the suture limbs are positioned within the notch 40. Proper positioning can be confirmed visually and/or by tactile sensation. One skilled in the art will recognize that the method can also be practiced using an outer guide that does not include a notch. Thus, in another embodiment (not shown), the inner guide 24 can be inserted into the lumen formed in the outer guide 22 such that the distal end 24b of the inner guide 24 terminates distal to the distal end 22b of the outer guide 22. With the inner and outer guides 24, 22 so positioned, the limbs of the suture can extend proximally along an outer surface of the inner guide 24 and will thereby be protected from being pinched between the outer guide 22 and the bone.

Figure 9:
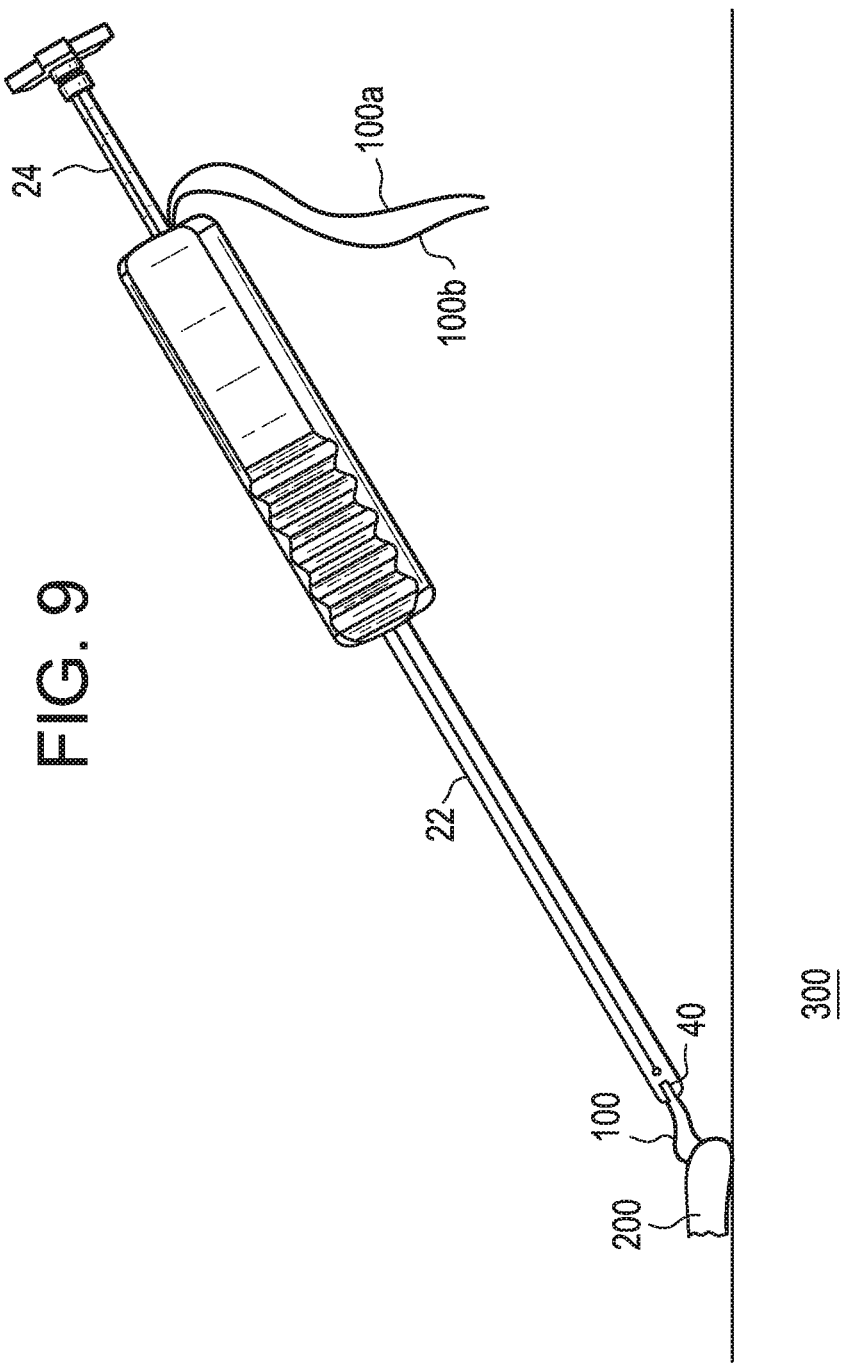
FIG. 9 is a side view of the outer guide of FIG. 8 with the inner guide being inserted therethrough.

As shown in FIG. 9, after the suture 100 is positioned within the outer guide 22, the inner guide 24 can be inserted into the lumen 26 formed of the outer guide 22 until the proximal end of the inner guide 24 is mated with a proximal end of the outer guide 22. As will be appreciated by a person skilled in the art, the inner and outer guides 24, 22 can have other features that indicate that the distal end of the inner guide 24 is positioned adjacent to the notch 40 without requiring a proximal end of the outer guide 22 to be mated to a proximal end of the inner guide 24. During insertion of the inner guide 24 into the outer guide 22, care should be taken to position the suture 100 between the outer surface of the inner guide 24 and the inner surface of the outer guide 22. This configuration serves to protect the limbs of the suture 100 during subsequent drilling, thereby decreasing the risk of damage to the suture 100. Following coupling of the inner guide 24 to the outer guide 22, the distal end 22b of the outer guide 22 is positioned to abut bone 300, as shown in FIG. 10. As so positioned, the suture adjacent to the distal end 22b of the outer guide 22 is arranged to pass through the notch 40 with the distal end 24b of the inner guide 24 being positioned adjacent to the notch 40.

Figure 11:
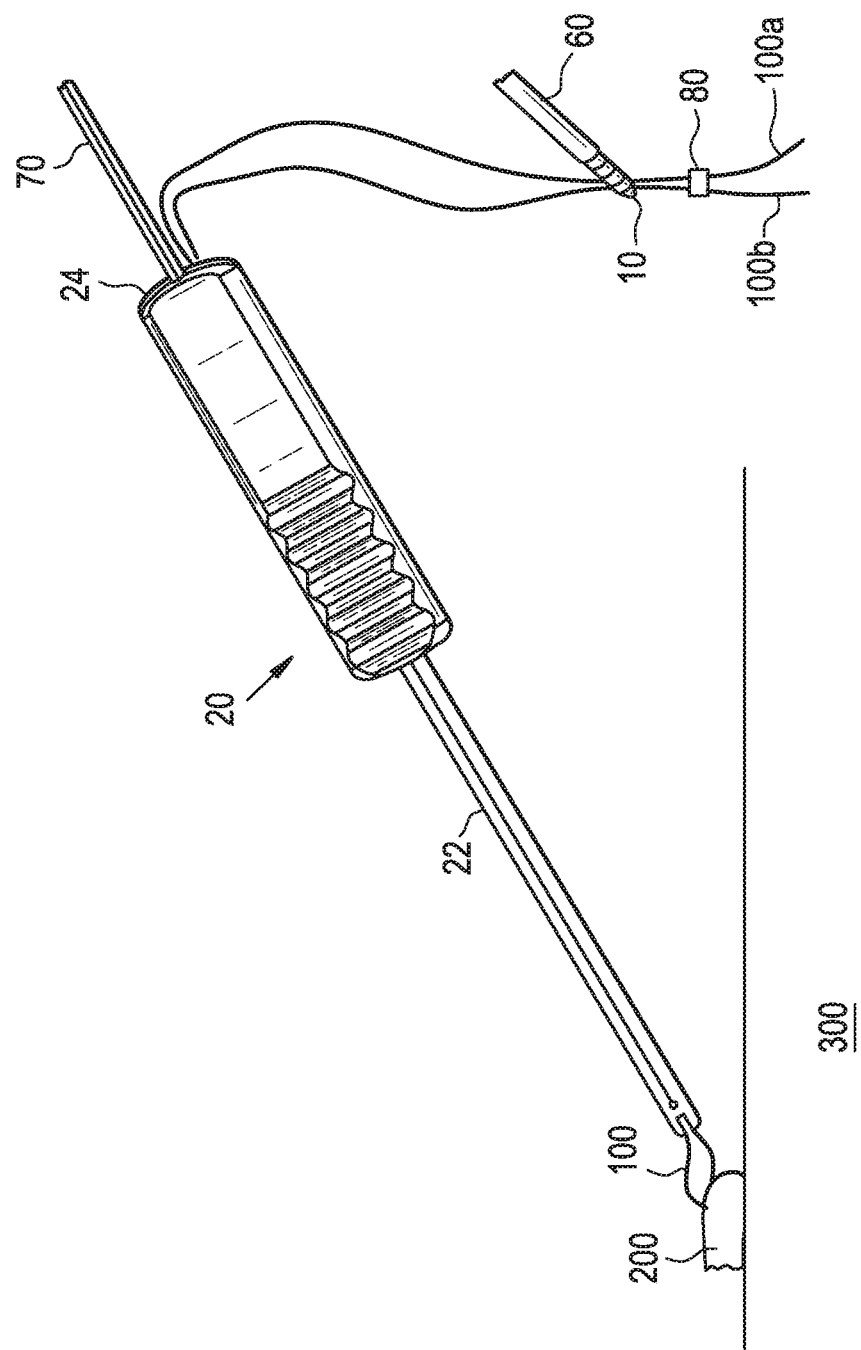
FIG. 11 is a side view of the drill guide with the anchor of FIG. 1 being attached to the inserter tool and having a suture threaded therethrough.

With the inner and outer guides 24, 22 so arranged, and the terminal ends of the suture 100 positioned outside of the drill guide 20, the suture can be threaded onto the suture anchor 10 using a threader tool (not shown) while the anchor remains outside of the patient's body. As will be appreciated by a person skilled in the art, the threader tool can have a variety of configurations. In one embodiment, the suture 100 is threaded onto the anchor 10 prior to drilling of the bone hole to prevent inadvertent movement of the drill guide 20 between the drilling and anchor insertion steps. Prior to or after threading, the threaded suture anchor 10 can be mated to a distal end 60b of the inserter tool 60, as shown in FIG. 11. Optionally, the portions of the suture 100 between the suture anchor 10 and the terminal ends 100a, 100b can be secured in clamping tool 80, which can prevent the suture 100 from being unintentionally pulled out from the anchor 10.

Figure 12:
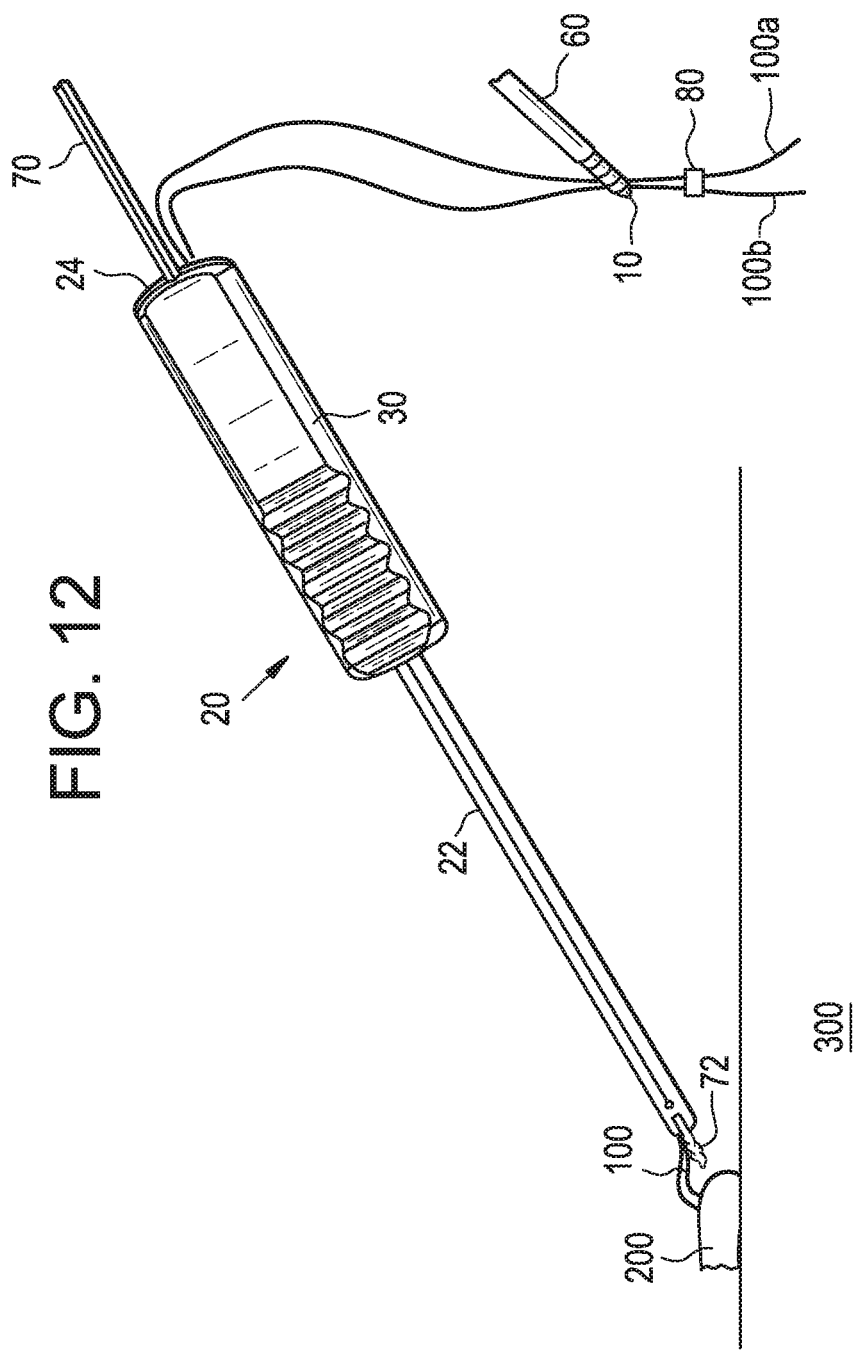
FIG. 12 is a side view of the drill of FIG. 6 being inserted through the outer guide.
Figure 13:
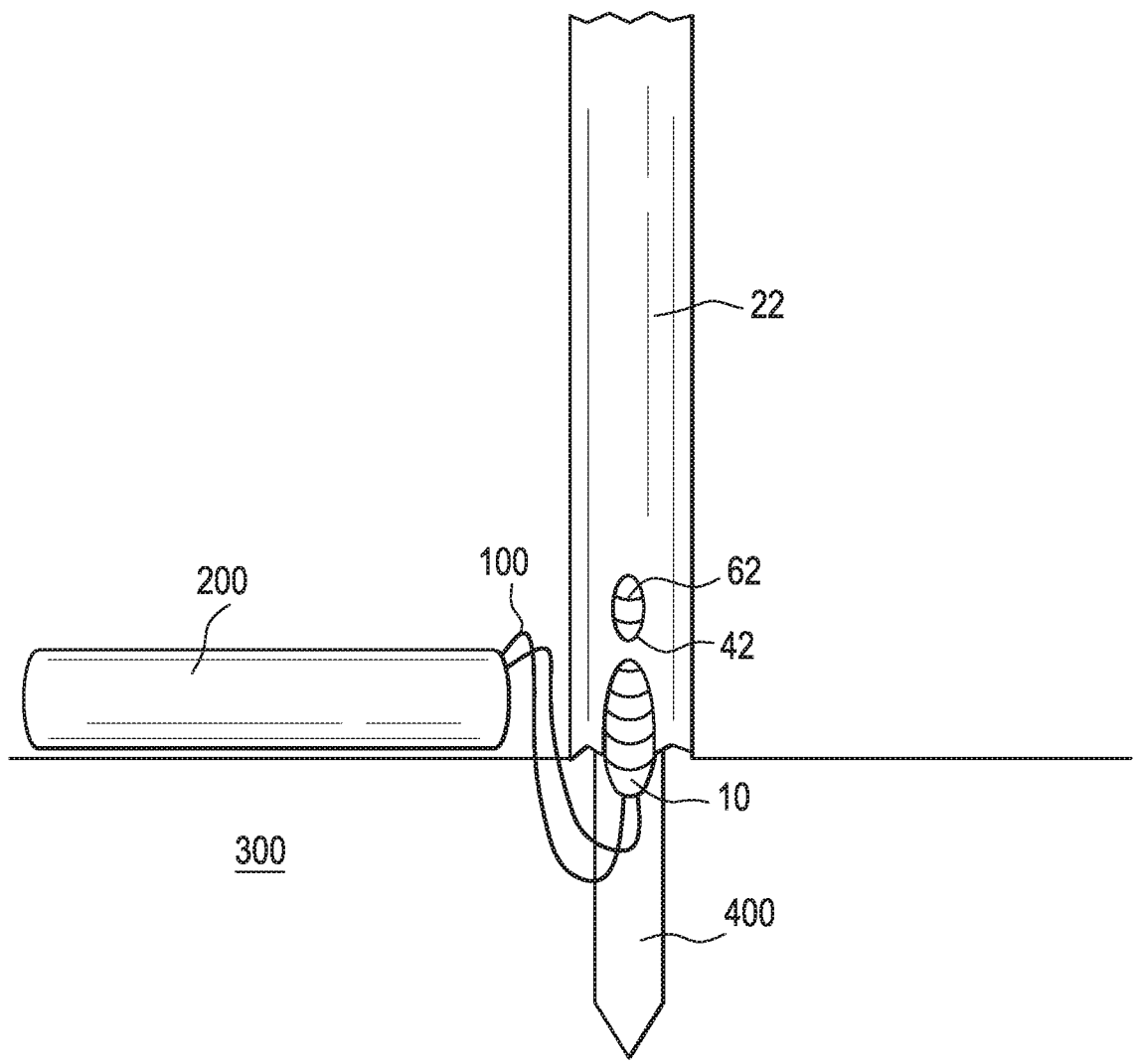
FIG. 13 is a side view of a distal portion of the drill guide showing the threaded suture anchor partially seated within the drilled hole.

With the inner and outer guides 24, 22 so positioned, and the suture 100 optionally threaded onto the suture anchor 10, a drill 70, having a cutting tip 72, can be inserted through the lumen 28 formed in the inner guide 24, as shown in FIG. 12. The cutting tip 72 can be rotated, manually or by a motor, to advance the cutting tip 72 through bone and form a hole (not shown). During drilling, a user can grasp the handle 30 of the drill guide 20, such as with two hands, to maintain the position of the drill guide 20 relative to the hole. After drilling, the drill 70 and the inner guide 24 can be removed from the lumen 26 of the outer guide 22. The inserter tool 60 can then be inserted through the lumen 26 of the outer guide 22 to deliver the suture anchor 10 to the hole 400. During this procedure, care should be taken to maintain the outer drill guide 22 in position while the inserter tool 60 is moved distally toward the drilled hole 400. As the inserter tool 60 is passed through the outer guide 22, the anchor 10 can slide along the suture 100 so that the terminal ends 100a, 100b remain outside of the patient's body. Continued alignment between the outer drill guide 22 and hole 400 as the suture anchor 10 is inserted ensures that a longitudinal axis L of the anchor 10 is aligned with the longitudinal axis L' of the hole, as shown in FIG. 13. Such alignment minimizes the risk of inserting the anchor 10 at an improper angle, which can damage the bone anchor 10 and/or cause the anchor 10 to fail.

A user can monitor the position of the anchor 10 within the outer guide 22 using a scoping device that is focused on one or more of the viewing windows, such as viewing window 42. In particular, FIG. 13 illustrates the distal end of the inserter tool 60 having a first laser line 62 formed on its outer surface such that when the anchor 10 is partially seated in the hole 400, the laser line 62 is visible from at least one viewing window. The positioning of the laser line 62 relative to the features on the outer guide 22, such as the notches and viewing windows, permits indirect monitoring of the positioning of the anchor 10 within the drilled hole 400. By way of non-limiting example, FIG. 13 shows that when the anchor 10 is partially seated in the drilled hole 400, the first laser line 62 can be visible in viewing window 42. Because the length of the anchor 10 and the positioning of the laser line 62 on the inserter tool 60 are known, when the first laser line 62 is located in the viewing window 42, the depth of the anchor 10 within the drilled hole 400 can be easily estimated. The positioning of the first laser line 62 within the window 42 can be confirmed using any visualization technique known in the art.

Figure 14:
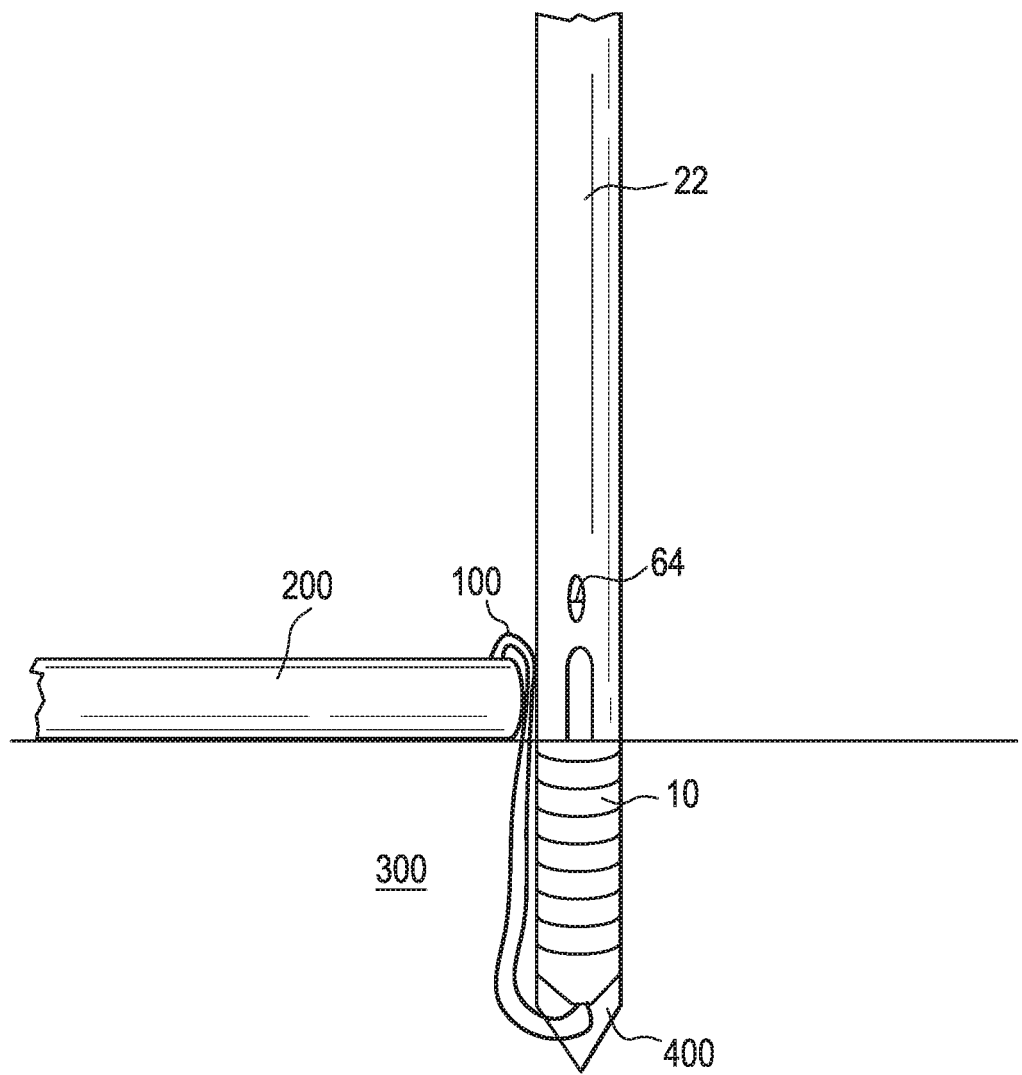
FIG. 14 is a side view of the drill guide of FIG. 12 with the anchor fully seated within the drilled hole.
Figure 15:
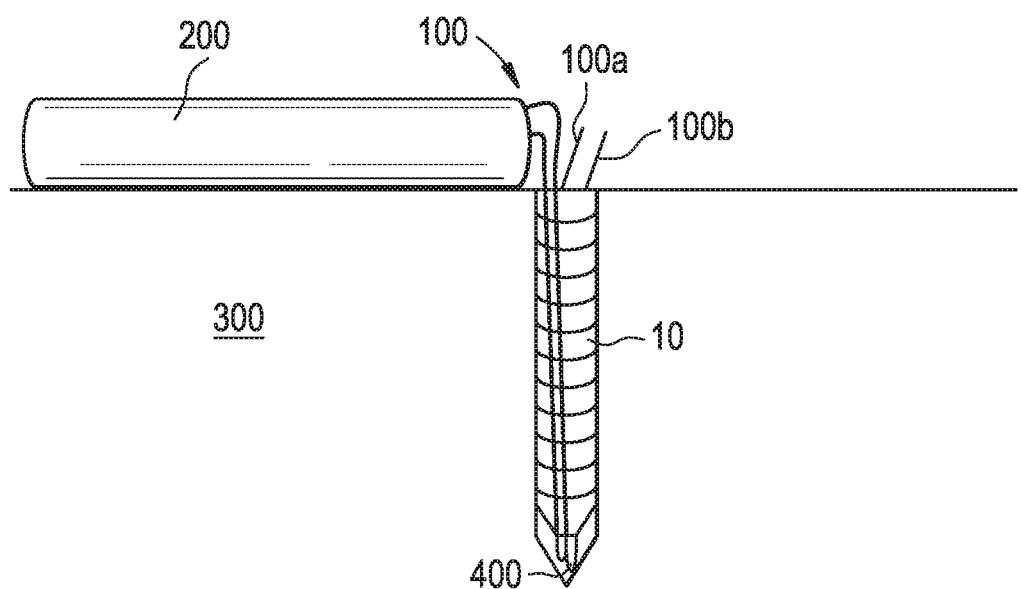
FIG. 15 is a side view of the suture anchor after the terminal ends of the suture are trimmed and the outer guide is removed from the attachment site.

Once the anchor 10 is partially seated within the drilled hole 400, the terminal ends 100a, 100b of the suture 100 can be pulled to tension the suture 100 and thereby pull the attached tissue 200 closer to the anchor 10, and thus, to the position of bone 300 to which it is to be secured. As will be appreciated by a person skilled in the art, the suture can also be tensioned prior to the anchor 10 being partially seated or fully seated in the drilled bole. The anchor 10 can be driven into the hole 400, such as by rotating and/or tapping the proximal end 60a of the inserter tool 60. This action serves to lock the suture 100 between an outer surface of the anchor 10 and an inner surface of the drilled hole 400. As will be appreciated by a person skilled in the art, the anchor 10 can lock the suture 100 in other ways, such as using a push-lock. As shown in FIG. 14, the second laser line 64 formed on the inserter tool 60 can be visible through at least one viewing window, e.g. window 24, once the anchor is fully seated within the hole 400. The positioning of the second laser line 64 can also be confirmed using any visualization technique known in the art. After the anchor 10 is fully seated in the hole 400, the outer drill guide 22 can be removed from the surgical site and the ends of the suture 100a, 100b can be trimmed and secured, as shown in FIG. 15.

The systems and methods described above can be used for a variety of tissue attachment procedures including, by way of non-limiting example, arthroscopic shoulder surgery. For example, the suture can be passed through the labrum and the drill guide can also be used to lever the humeral head away from the glenoid cavity to gain access to the glenoid rim prior to drilling the bone.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    a first elongate tubular member having an inner lumen extending longitudinally therethrough, the first elongate tubular member having a notch formed through a sidewall thereof, the notch extending proximally from a distal end of the first elongate tubular member along a partial longitudinal length thereof, the notch being in communication with the inner lumen to allow a suture within the inner lumen to extend outside the first elongate tubular member through the notch, the first elongate tubular member having a first alignment feature, a proximal end of the first elongate tubular member has an opening formed therein that defines an open proximal end of the inner lumen of the first elongate tubular member, and the first elongate tubular member being configured to be advanced into a body of a patient until the distal end of the first elongate tubular member engages bone; and
    a second elongate tubular member having an inner lumen extending longitudinally therethrough, the second elongate tubular member having a second alignment feature, and, with the distal end of the first elongate tubular member engaging the bone, the second elongate tubular member is configured to be inserted into the inner lumen of the first elongate tubular member through the open proximal end of the inner lumen of the first elongate tubular member and advanced distally along the inner lumen of the first elongate tubular member until the first alignment feature aligns with the second alignment feature, thereby indicating that a distal end of the second elongate tubular member is positioned adjacent to the notch within the inner lumen of the first elongate tubular member;

wherein the first alignment feature is a mating feature at the proximal end of the first elongate tubular member, the second alignment feature is a mating feature at a proximal end of the second elongate tubular member, and the first and second alignment features align by coming into mating contact with one another.

2. The system of claim 1, further comprising a bone drill configured to be inserted into the inner lumens of the first and second elongate tubular members with the distal end of the second elongate tubular member positioned adjacent to the notch within the inner lumen of the first elongate tubular member.

3. The system of claim 1, further comprising a suture configured to
extend longitudinally along the first elongate tubular member within the inner lumen of the first elongate tubular member in a gap formed between an inner wall of the first elongate tubular member and an outer wall of the second elongate tubular member and
extend outside the first elongate tubular member through the notch.

4. The system of claim 2, further comprising a suture anchor configured to be coupled to the suture and, while coupled to the suture, configured to be advanced distally through the inner lumens of the first and second elongate tubular members.

5. A surgical method, comprising:
positioning an outer guide within a body of a patient such that a distal end of the outer guide engages bone;
after the positioning of the outer guide within the body of the patient such that the distal end of the outer guide engages bone, inserting a distal end of an inner guide into an inner lumen of an outer guide such that a suture in the inner lumen of the outer guide is positioned between an outer surface of the inner guide and an inner surface of the outer guide, the inner lumen extending longitudinally along the outer guide, the outer guide having a notch formed in a side wall thereof at the distal end of the outer guide, and the suture extending through the notch from inside the inner lumen;
advancing the distal end of the inner guide distally along the inner lumen of the outer guide until the distal end of the inner guide is positioned adjacent to the notch;
with the distal end of the inner guide positioned adjacent to the notch and with the distal end of the outer guide engaging the bone, advancing a drill distally along an inner lumen of the inner guide and the inner lumen of the outer guide until a distal end of the drill exits the inner lumen of the outer guide; and
rotating the drill within the inner lumens of the inner guide and outer guide to cut the bone.

6. The method of claim 5, wherein the distal end of the inner guide is advanced distally along the inner lumen of the outer guide until an alignment feature of the inner guide indicates that the distal end of the inner guide is positioned adjacent to the notch.

7. The method of claim 6, wherein the alignment feature indicates that the distal end of the inner guide is positioned adjacent to the notch by the alignment feature of the inner guide coming into contact with an alignment feature at a proximal end of the outer guide.

8. The method of claim 6, wherein the alignment feature of the inner guide is a mark formed on the inner guide, and the alignment feature indicates that the distal end of the inner guide is positioned adjacent to the notch by becoming visible through a viewing window in the side wall of the outer guide during the advancement of the distal end of the inner guide distally along the inner lumen of the outer guide.

9. The method of claim 5, further comprising coupling the suture to soft tissue before the rotation of the drill.

10. The method of claim 5, wherein the suture positioned between the outer surface of the inner guide and the inner surface of the outer guide has terminal ends extending proximally from a proximal end of the outer guide.

11. The method of claim 5, wherein the drill cuts a hole in the bone, and the method further comprises advancing an anchor along the inner lumens of the inner guide and outer guide and into the hole, the anchor being coupled to the suture.

12. The method of claim 11, wherein the suture is coupled to soft tissue, and the method further comprises tensioning the suture to pull the soft tissue closer to the anchor in the hole.

13. The method of claim 5, wherein the inserting of the distal end of the inner guide into the inner lumen of the outer guide includes, after the outer guide has been positioned within the body of the patient, introducing the distal end of the inner guide into an opening in a proximal end of the outer guide that defines an open proximal end of the inner lumen of the outer guide.

14. A surgical method, comprising:
positioning an outer guide within a body of a patient such that a distal end of the outer guide engages bone;
inserting a distal end of an inner guide into an inner lumen of an outer guide such that a suture in the inner lumen of the outer guide is positioned between an outer surface of the inner guide and an inner surface of the outer guide, the inner lumen extending longitudinally along the outer guide, the outer guide having a notch formed in a side wall thereof at the distal end of the outer guide, and the suture extending through the notch from inside the inner lumen;
advancing the distal end of the inner guide distally along the inner lumen of the outer guide until the distal end of the inner guide is positioned adjacent to the notch;
with the distal end of the inner guide positioned adjacent to the notch and with the distal end of the outer guide engaging the bone, advancing a drill distally along an inner lumen of the inner guide and the inner lumen of the outer guide until a distal end of the drill exits the inner lumen of the outer guide;
rotating the drill within the inner lumens of the inner guide and outer guide to cut the bone;
after the drill is rotated to cut the bone, removing the drill from the inner lumens of the inner guide and outer guide and removing the inner guide from the inner lumen of the outer guide; and
after the removal of the drill and the removal of the inner guide, inserting an inserter tool into the inner lumen of the outer guide and advancing the inserter tool distally along the inner lumen of the outer guide such that an anchor coupled to a distal end of the inserter tool is advanced distally into the bone.

15. The method of claim 14, wherein the distal end of the inner guide is advanced distally along the inner lumen of the outer guide until an alignment feature of the inner guide indicates that the distal end of the inner guide is positioned adjacent to the notch; and
the alignment feature indicates that the distal end of the inner guide is positioned adjacent to the notch by the alignment feature of the inner guide coming into contact with an alignment feature at a proximal end of the outer guide.

\* \* \* \* \*